(12) United States Patent
Preiss et al.

(10) Patent No.: US 10,524,821 B2
(45) Date of Patent: Jan. 7, 2020

(54) SYSTEM AND METHOD FOR MORCELLATION OF TISSUE

(71) Applicant: LUMENIS LTD., Yokneam Ilit (IL)

(72) Inventors: Assaf Preiss, Shimshit (IL); Silvio Rosen, Yokneam Ilit (IL); Yoav Nevo, Yokneam Ilit (IL)

(73) Assignee: LUMENIS, Yokneam (IL)

( * ) Notice: Subject to any disclaimer, the term of this patent is extended or adjusted under 35 U.S.C. 154(b) by 161 days.

(21) Appl. No.: 15/710,316

(22) Filed: Sep. 20, 2017

(65) Prior Publication Data

US 2018/0085138 A1 Mar. 29, 2018

Related U.S. Application Data

(60) Provisional application No. 62/398,583, filed on Sep. 23, 2016.

(51) Int. Cl.
*A61B 17/32* (2006.01)
*A61B 17/3205* (2006.01)

(52) U.S. Cl.
CPC .. *A61B 17/32002* (2013.01); *A61B 17/32056* (2013.01); *A61B 2017/320032* (2013.01)

(58) Field of Classification Search
CPC ............ A61B 17/32; A61B 17/320016; A61B 17/32002; A61B 17/32056; A61B 2017/320024; A61B 2017/320028; A61B 2017/320032
See application file for complete search history.

*Primary Examiner* — Melanie R Tyson
(74) *Attorney, Agent, or Firm* — Isus Intellectual Property PLL; Anthony Jason Mirabito

(57) ABSTRACT

A device for selectively grasping and cutting tissue includes an outer tube having a longitudinal axis and an open proximal end and an open distal end; also an inner tube within the outer tube, the inner tube having a longitudinal axis and an open distal end and an open proximal end; as well as a cup-shaped cutting member mounted to the distal end of the outer tube, the cutting member being larger in diameter than the diameter of the outer tube, the cutting member including one or more cutting surfaces around the lip of the cup-shaped cutting member, the one or more cutting surfaces facing in a distal direction; also, a cylindrical cup-shaped cutting member mounted to the distal end of the inner tube; the cutting member including one or more cutting surfaces mounted around the lip of the cylindrical cup-shaped cutting member facing in a proximal direction; and, the inner tube is of a diameter to be slidably movable within the outer tube; whereby moving the inner tube alternately in distal and proximal directions along the longitudinal axis causes the one or more cutting surfaces of the inner tube to approach and distance themselves from the one or more cutting surfaces of the outer tube, and, whereby tissue situated between the inner tube and the outer tube is grasped and cut.

12 Claims, 20 Drawing Sheets

| NEW BLADES ASSEMBLY CONFIGURATION | DESCRIPTION | WORKING TIME [min.] TO CONSUME MEAT CUBE OF 15gr. | WORKING TIME [min.] TO CONSUME MEAT CUBE OF 40gr |
|---|---|---|---|
| 1. | OUTER BLADE: PLAIN<br>INNER BLADE: PLAIN | 02:15 | 07:09<br>(+01:20)<br>(X2) |
| 2. | OUTER BLAND: PLAIN<br>INNER BLADE: TEETH | 02:30 | 07:57<br>(+01:15) |
| 3. | OUTTER BLADE: PLAIN<br>INNER BLADE: SHARP | 02:11 | 07:52<br>(+0:30) |
| 4. | OUTER BLADE: PLAIN<br>INNER BLADE: ROUND | 01:45 | 06:22<br>(+0:50)<br>(X3) |

FIG.8A

| NEW BLADES ASSEMBLY CONFIGURATION | | DESCRIPTION | WORKING TIME [min.] TO CONSUME MEAT CUBE OF 15gr. | WORKING TIME [min.] TO CONSUME MEAT CUBE OF 40gr |
|---|---|---|---|---|
| 5. | | OUTER BLADE: PLAIN LONG INNER BLADE: PLAIN | 02:50 | 09:25 (+0:04) (X3) |
| 6. | | OUTER BLAND: PLAIN LONG INNER BLADE: TEETH | 01:55 | 04:38 (+0:45) |
| 7. | | OUTER BLADE: PLAIN LONG INNER BLADE: SHARP | 02:10 | 05:58 (+0:40) |
| 8. | | OUTER BLADE: PLAIN INNER BLADE: ROUND | 01:53 | 06:50 (+0:40) (X5) |

FIG.8B

| NEW BLADES ASSEMBLY CONFIGURATION | DESCRIPTION | WORKING TIME [min.] TO CONSUME MEAT CUBE OF 15gr. | WORKING TIME [min.] TO CONSUME MEAT CUBE OF 40gr |
|---|---|---|---|
| 9. | OUTER BLADE: TEETH<br>INNER BLADE: PLAIN | 02:35 | 06:05<br>(+01:35) |
| 10. | OUTER BLAND: TEETH<br>INNER BLADE: TEETH | 02:01 | 06:03<br>(+0:55) |
| 11. | OUTER BLADE: SHARP<br>INNER BLADE: PLAIN | 01:47 | 05:00<br>(+0:50) |
| 12. | OUTER BLADE: SHARP<br>INNER BLADE: SHARP | 02:17 | 05:01<br>(+01:05) |

Figure 8C

| NEW BLADES ASSEMBLY CONFIGURATION | DESCRIPTION | WORKING TIME [min.] TO CONSUME MEAT CUBE OF 15gr. | WORKING TIME [min.] TO CONSUME MEAT CUBE OF 40gr |
|---|---|---|---|
| 13.  | OUTER BLADE: ROUND INNER BLADE: PLAIN | 01:37 | 06:05 (+01:35) (X1) |
| 14.  | OUTER BLAND: ROUND INNER BLADE: ROUND | 02:02 | 07:02 (+01:20) (X1) |
| 15.  | OUTTER BLADE: ROUND INNER BLADE: TEETH | | 03:42 (+0:35) |
| 16.  | OUTTER BLADE: SHARP INNER BLADE: TEETH | | 03:22 (+0:25) |

SYSTEM AND METHOD FOR MORCELLATION OF TISSUE

RELATED APPLICATIONS

This application is related to and claims priority to U.S. Provisional Application Ser. No. 62/398,583, filed Sep. 23, 2016, the entire disclosure of which is herein incorporated by reference.

BACKGROUND OF THE PRESENT INVENTION

In certain laparoscopic or endoscopic surgeries, such as the laser enucleation of the prostate, hysterectomy or other procedures, there is a need to extract masses of tissue from a surgical site to outside of the body through a channel formed in an endoscope. That channel is generally known as and will be referred to herein as a working channel.

A morcellation device is one type of instrument frequently used to cut masses of tissue into smaller pieces and to then to extract these smaller pieces through a channel within the morcellator. The morcellator may have (and usually does have) a number of channels whose various uses or functions are described herein.

In the prior art, rotational morcellators, such as disclosed in U.S. Pat. No. 8,998,887 or linear morcellators, such as disclosed in U.S. Pat. No. 8,945,021 are known. One common feature of these morcellation devices is the application of negative pressure through a channel of the morcellator. The negative pressure induced pulls a tissue mass toward an opening located in the distal tip of the morcellator. The negative pressure further assures mechanical contact between the tissue mass and one or more moving blades located in the opening. Rotational or linear blades move inside a working channel of the morcellator and cut the tissue mass into smaller pieces which can then be suctioned out of the body through a channel in the morcellator.

Different tools may be inserted through the endoscope and into a surgical site, such as graspers, suturing devices, lasers, knifes etc. The endoscope itself is inserted into the body through a natural orifice or through an incision site. In a laser enucleation procedure, for example, an ureteroscope is inserted through the urethra into the bladder. A waveguide is then inserted through the scope into the bladder and up to the prostate in order to deliver the laser radiation to cut pieces of the prostate, in the case, for example, of benign prostate hyperplasia. Masses of prostate tissue then fall into the bladder and these masses need to be removed from the patient's body through a working channel of the endoscope. These tissue masses, however, may be too large to fit and move through the working channel of the endoscope unless cut into smaller pieces. Therefore, a morcellation device may then be applied to first cut the tissue mass in the bladder and only then to use a suction channel to extract them from the patient.

The level of vacuum in the working channel of the morcellator, among other parameters, controls the efficacy of the morcellator for pulling tissue masses floating in the bladder into its opening and the level of mechanical contact a tissue mass establishes with the morcellator's moving blades. However, there is a practical limit to the vacuum level which can be created inside the bladder. As a result, often the suction or vacuum forces designed to pull tissue masses toward the opening in the morcellator shaft are insufficient and, further, there may be insufficient mechanical coupling during morcellation between a tissue mass and the moving blades. As a result, expensive time is wasted chasing tissue masses which become separated from the morcellator during the cutting process.

A variety of solutions are suggested in the prior art for dealing with these problems. One set of possible solutions is the implementation of different blade designs and geometries, such as disclosed in US Patent application 2008039880, which discloses a round blade with grooves which are designed to better hold the tissue and keep it in place. Serrated blades along or across a morcellator's opening are disclosed in US Patent application 2015305765, WO16018457, U.S. Pat. No. 9,433,437, or in US patent application no. 2016235469 to provide an improved cutting mechanism.

Also known in the prior art are baskets and snares mechanisms, such as disclosed, for example, in U.S. Pat. No. 8,435,237 or US Patent application no. 2016045214, which are designed to be inserted in a folded position through an endoscope or a morcellator into a surgical site and to collect tissue debris in an extended position distally to the surgical instrument. Snaring and wire-cutting loops are also known and are disclosed, for example, in US Patent application no. 20122289971. The foregoing US patent application discloses an extendable loop wire which is designed to hold a tissue mass in the vicinity of a surgical grasper. Yet, an improved mechanism to collect, hold and cut tissue masses effectively within a surgical site is still desired and needed. It is one aspect of the present invention to provide a morcellation system with improved efficiency to remedy the above shortcomings of the prior art devices.

SUMMARY OF THE PRESENT INVENTION

In an aspect, a device for selectively grasping and cutting tissue includes an outer tube having a longitudinal axis and an open proximal end and an open distal end; also an inner tube within the outer tube, the inner tube having a longitudinal axis and an open distal end and an open proximal end; as well as a cup-shaped cutting member mounted to the distal end of the outer tube, the cutting member being larger in diameter than the diameter of the outer tube, the cutting member including one or more cutting surfaces around the lip of the cup-shaped cutting member, the one or more cutting surfaces facing in a distal direction; also, a cylindrical cup-shaped cutting member mounted to the distal end of the inner tube; the cutting member including one or more cutting surfaces mounted around the lip of the cylindrical cup-shaped cutting member facing in a proximal direction; and, the inner tube is of a diameter to be slidably movable within the outer tube; whereby moving the inner tube alternately in distal and proximal directions along the longitudinal axis causes the one or more cutting surfaces of the inner tube to approach and distance themselves from the one or more cutting surfaces of the outer tube, and, whereby tissue situated between the inner tube and the outer tube is grasped and cut.

In another aspect, the cutting surfaces on one or both of the inner and outer tubes are either straight or serrated. The device further may include an endoscopic tube having a distal end and a proximal end, the endoscopic tube having a working channel having a diameter greater than that of the outer tube, whereby the proximal end of the working channel of the endoscopic tube accepts the distal end of the outer tube and the distal end of the outer tube accepts the proximal end of the inner tube through the distal end of the working channel.

In a further aspect, the cup-shaped cutting members of the outer and the inner tubes may have a diameter no greater than that of the endoscopic tube, whereby the overall profile of the endoscopic and cup-shaped members present an overall diameter no greater than that of the endoscopic tube. Also, the inner tube just proximal of the cup-shaped cutting member may include a cutout cavity along the longitudinal axis of the inner tube, further including a second cutting surface facing in a proximal direction within the cutout to grasp and cut tissue with the cutout. Further, the second cutting surface may be one of straight or serrated.

In yet another aspect, the outer tube just distal of the cup-shaped cutting member may include a cutout along the longitudinal axis of the inner tube, further comprising a grasping device which grasps and holds tissue during cutting by moving the inner tube in a proximal direction along its longitudinal axis. Further, the grasping device may include a one or pair of wires which engage and hold tissue portion prior to and during cutting by the one or more cutting surfaces on the inner and outer tubes. Also, the grasping device may include a looped wire that grasps and holds a tissue portion prior to and during cutting by the one or more cutting surfaces on the inner and outer tubes. A vacuum device which pulls tissue into the inner tube cavity may be provided.

In an aspect, a method of grasping and cutting tissue includes the steps of: providing an outer tube having a longitudinal axis and an open proximal end and an open distal end; providing an inner tube within the outer tube, the inner tube having a longitudinal axis and an open distal end and an open proximal end; providing a cup-shaped cutting member mounted to the distal end of the outer tube, the cutting member being larger in diameter than the diameter of the outer tube, the cutting member including one or more cutting surfaces around the lip of the cup-shaped cutting member, the one or more cutting surfaces facing in a distal direction; further, providing a cylindrical cup-shaped cutting member mounted to the distal end of the inner tube; the cutting member including one or more cutting surfaces mounted around the lip of the cylindrical cup-shaped cutting member facing in a proximal direction. The inner tube may be of a diameter to be slidably movable within the outer tube; the method further includes the step of moving the inner tube alternately in distal and proximal directions along the longitudinal axis, the moving causing the one or more cutting surfaces of the inner tube to approach and distance themselves from the one or more cutting surfaces of the outer tube; whereby tissue situated between the inner tube and the outer tube is grasped and cut. The method may further include the step of employing a vacuum device to pull tissue into the inner tube cavity.

BRIEF DESCRIPTION OF THE DRAWINGS

FIGS. 8A through 8D illustrate different blade geometries and different blade pairings and different cavity sizes.

FIGS. 9 through 15A, 15B and 15C illustrate different tissue grasping and holding device embodiments for use with the morcellator devices of the present invention.

DETAILED DESCRIPTION OF THE PRESENT INVENTION

A working channel diameter in a laparoscope, endoscope or any other surgical scope such as for example, uretroscope, cystoscope or naphroscope, is, as a practical matter, limited in size due to, for example, the need for it to be inserted into body orifices or target tissue dimensions. Further, at any given time, additional other instruments may be required to be inserted through the instrument's channel or channels simultaneously. Therefore, surgical instruments which are designed to be inserted through such working channels are very limited in size and shape. The working channel of the scope is designed to be used with different instruments for performing surgical procedures. At different stages of the procedure, different instruments are inserted into the surgical site. In case of a multiple incision procedure, more than one working channel may be available for the physician and multiple tools may be used together. Some surgical instruments are designed to be inserted in a reduced folded form into the channel and allowed to expand once they reach the distal tip of the scope. This requires specific solutions to transform the shape of these instruments from a folded position to an unfolded position. This transformation may be "spontaneous", for example, by using shape memory materials or by a control mechanism which allows the control of an instrument located in the distal tip of the scope from its proximal site by a physician.

Other channels present in the scope may contain other devices which are purposed to provide illumination, visualization and irrigation or other fluid supply. These devices are crucial to maintain an appropriate surgical environment in order that the physician be able to effectively perform the surgery. The room within the scope that the above-mentioned parallel channels occupy within the scope further increase the problem of having sufficient space within the scope. Usually, these parallel channels and the instruments which occupy these channels, are characterized by a round cross section. As a result there are "dead zones" in the scope located in the space(s) in between the round cross sectional channels which are not used. It is one aspect of the present invention to provide a solid cutting instrument which is not a flexible or foldable and yet wider and bigger than available cross section of the scope working channel.

Figure 1B:
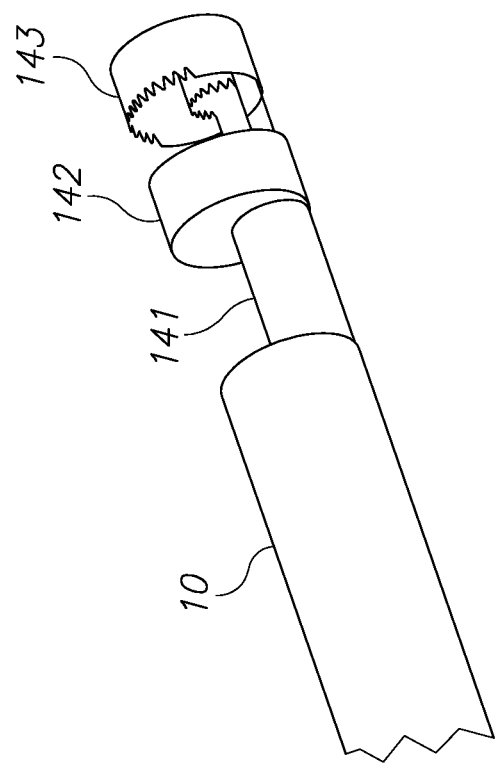
FIGS. 1A-1D illustrate the placement of the device of the resent invention within an endoscope.
Figure 1A:
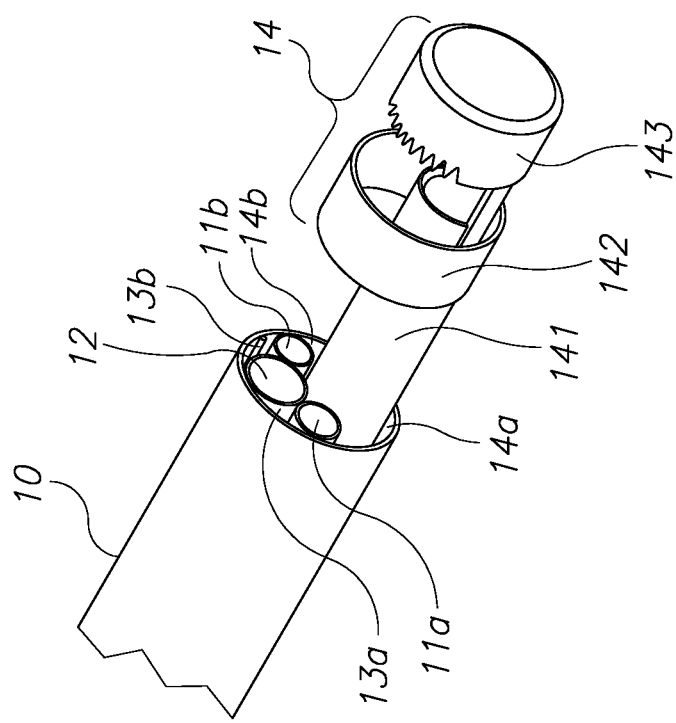
Figure 1C:
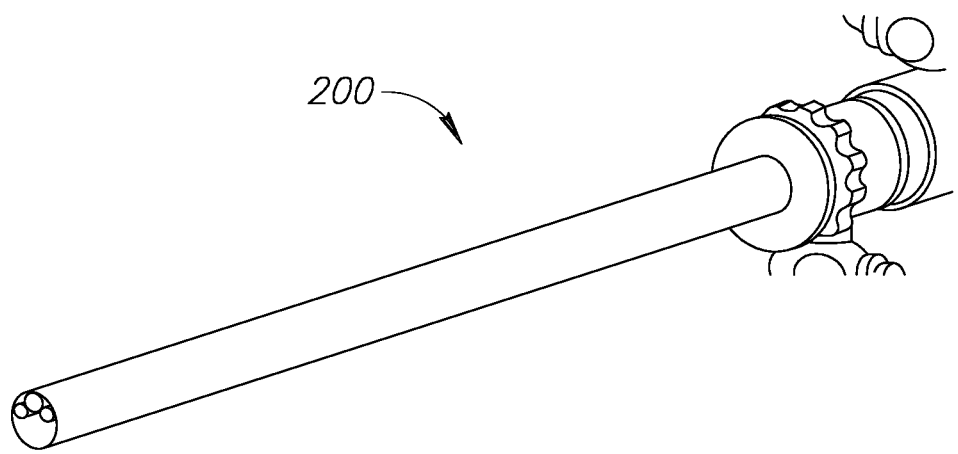
Figure 1D:
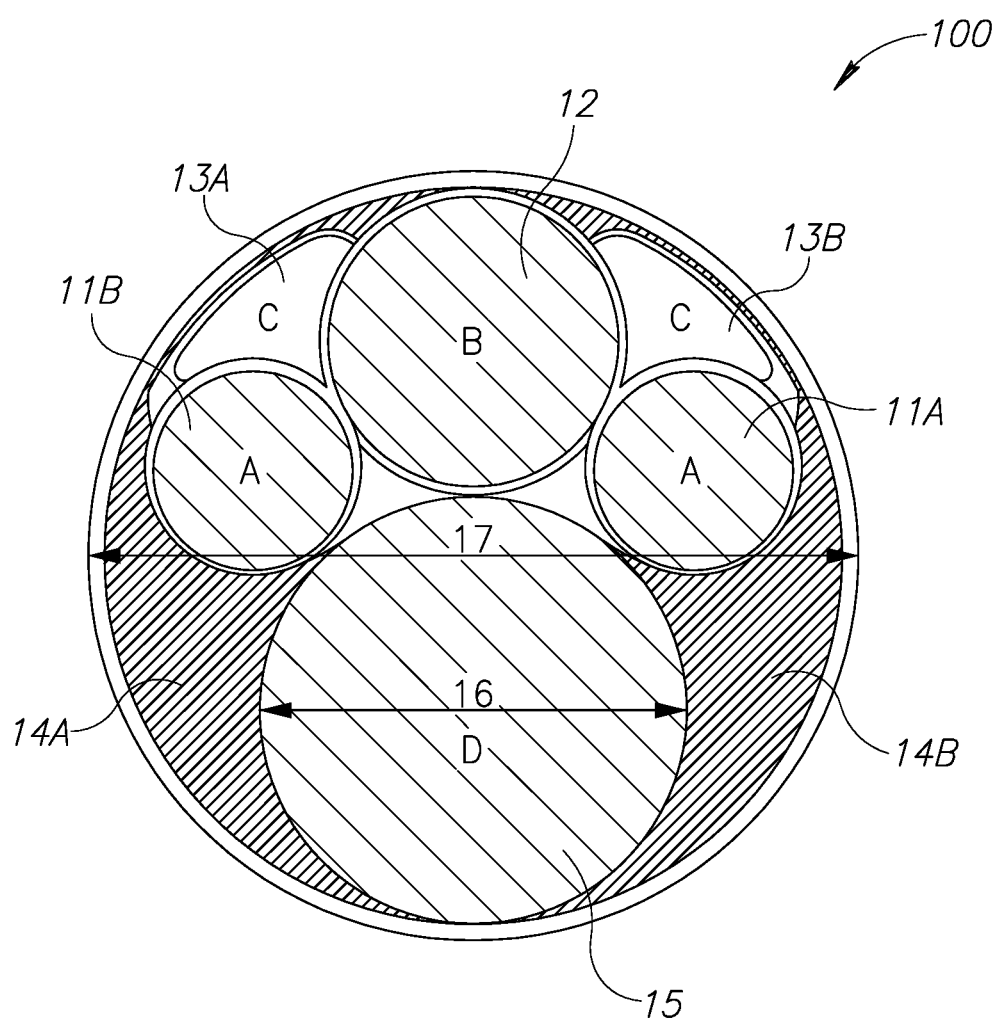
Figure 2:
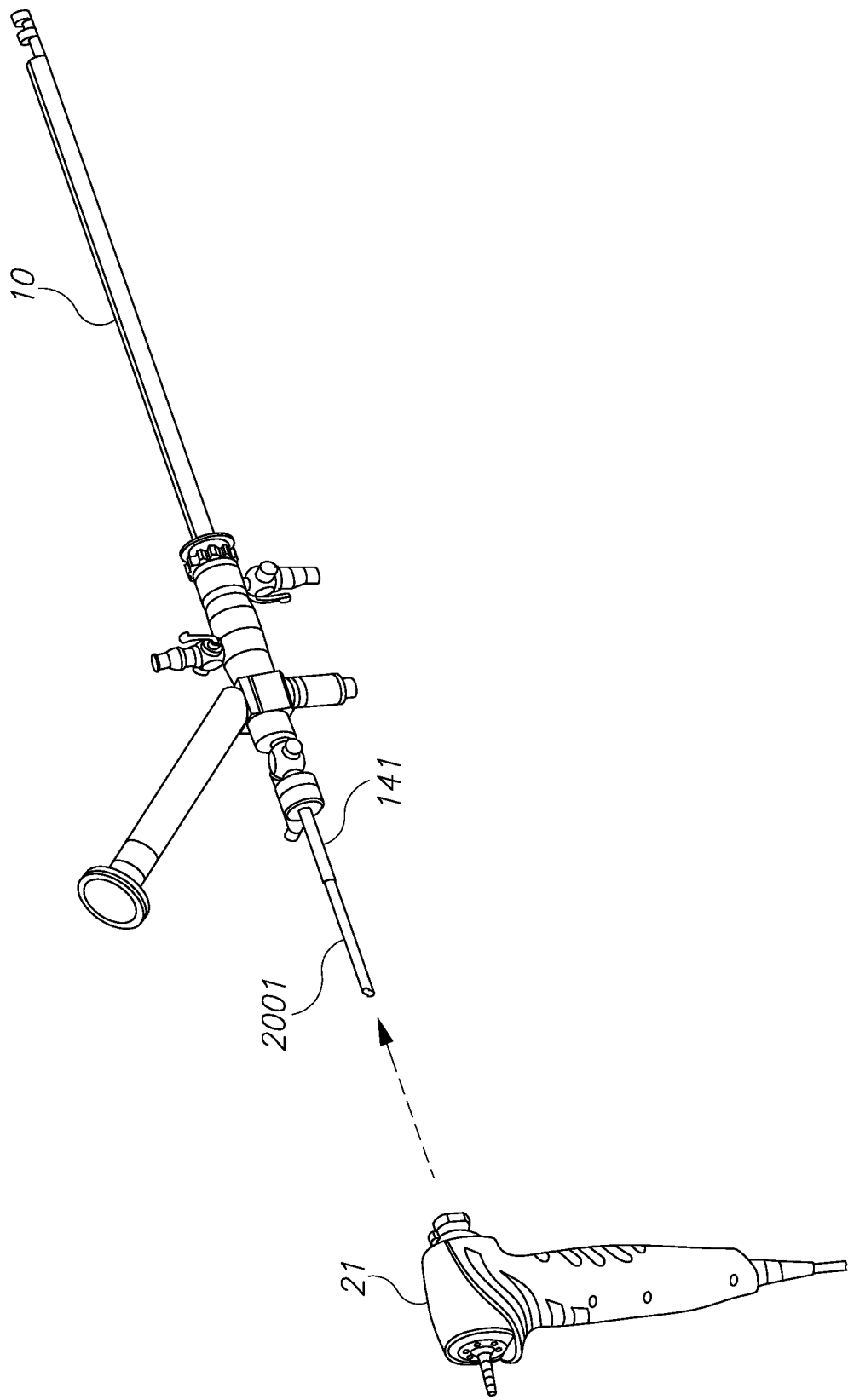
FIG. 2 illustrates a combination of a nephroscope with its handpiece control.

Referring now to FIGS. 1A through 1D, those figures illustrate the general structure of a nephroscope 10, which has a first illumination channel 11a, a second optional illumination channel 11b, and a visualization channel 12. A morcellator 14 is positioned in the working channel of the scope. As can be seen best in the FIG. 1D, due to the round nature of these channels, dead spaces 13a and 13b are located between these channels. Dead spaces 13a, 13b around and between channels 11a, 11b and 12 may be used as inlet ports for the provision of, for example, an irrigation fluid. Dead spaces around the working channel 15 for the morcellator, shown as two channels 14a and 14b, are usually not in use. The working channel of the endoscope however, is limited to a diameter 16 and is large enough only to insert the shaft 141 of the morcellator, as may be seen in FIGS. 1A and 1B. The distal tip of the shaft 141 comprises an external ring 142 which is configured to hold and cut tissue mass and an external blade 143 which is configured to hold and cut a tissue mass. These structures have larger diameters than the diameter of the working scope 15 and therefore cannot be inserted through the working channel of scope in a rigid form. However, as can be seen in FIGS. 1A and 1B, the diameter of scope 10 is larger than that of the shaft 141. Moreover, the diameter 17 of scope 10 dictates the size of an incision required should the scope not be inserted through a natural orifice in the body. Therefore, according to this aspect of the invention, there is provided a modular morcellator which consists of an elongated shaft member 141, as can be seen in FIG. 2 and a handpiece 21. Shaft member 141 is configured to be inserted into a working channel of a scope from its distal end rather than its proximal end and before the scope is inserted into the body through a trocar. Proximal end 2001 of shaft member 141 extends out of the proximal end of scope 10 and is configured to be connected to handpiece 21.

Referring now again to FIGS. 1A and 1B, the distal tip of a morcellator 14 which consists of elements 142 and 143 has a larger diameter than the diameter 16 of the working channel 15 of scope 10 and may be approximately the same diameter as that of scope 10. According to this aspect of the invention, solid and rigid tissue holders and cutting blades located at a distal end of a morcellator, having a larger diameter than the diameter of the working channel of a scope 10 may be used. Dead zones 13a, 13b, 14a and 14b or channels 11, 12 or 13 will no longer consume expensive real estate available for the distal tip of shaft 141 of the morcellator 14.

Figure 3:
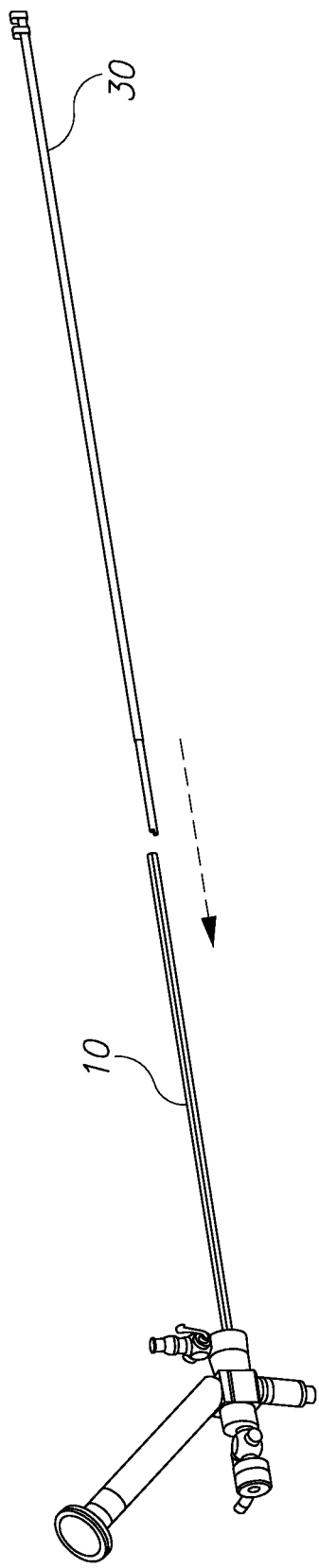
FIG. 3 illustrates a method of insertion of the device of the present invention into the distal end of an endoscope.
Figure 4:
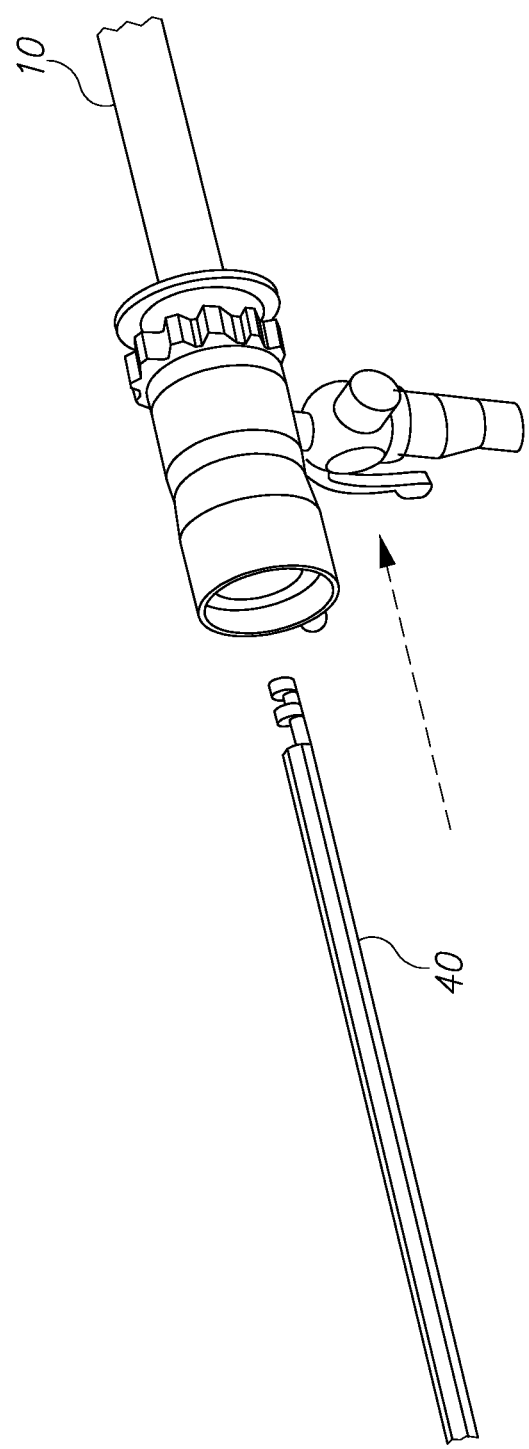
FIG. 4 illustrates how the morcellator device of the present invention may be used externally and in conjunction with an outer sheath.

FIG. 3 shows a reverse assembly of a morcellator shaft member 30 into scope 10 as described above. As shown in FIG. 4, morcellator 40 may be used externally and in conjunction with an outer sheath which includes channels 11a, 11b and 12 of FIG. 1D. FIG. 1D shows a cross-section view 100 of endoscope 200. Irrigation channels 13a, 13b make use of dead spaces located between illumination channels 11a and 11b and visualization channel 12. However, dead areas 14a, 14b located around the endoscope working channel 15 are not utilized. Any surgical instrument which is designed to pass through working channel 15 cannot have a diameter larger than the diameter 16 of working channel 15. However, endoscope 200 diameter 17 is much bigger. A surgical instrument having a similar diameter to diameter 17 will not increase the cross sectional foot print of the scope, but it cannot be delivered into the surgical site through working channel 15 due its smaller diameter 16. It is one aspect of the present invention to provide a modular morcellator and a reverse assembly method having a morcellator tip 14 which is larger than diameter 16.

Figure 5B:
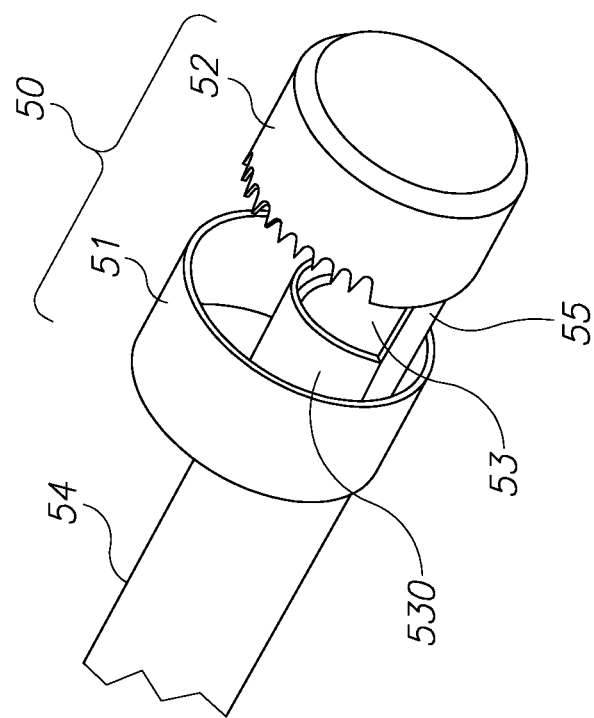
FIGS. 5A and 5B illustrate structures for cutting devices for the morcellator of the present invention.
Figure 5A:
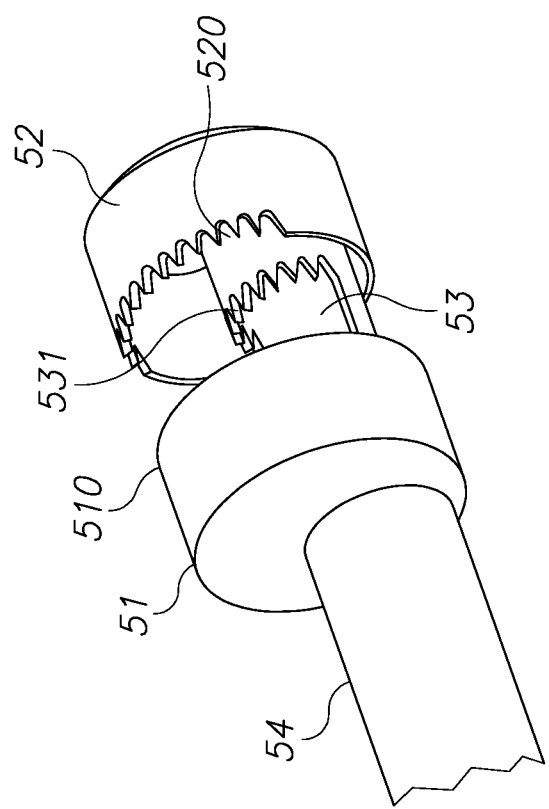
Figure 6B:
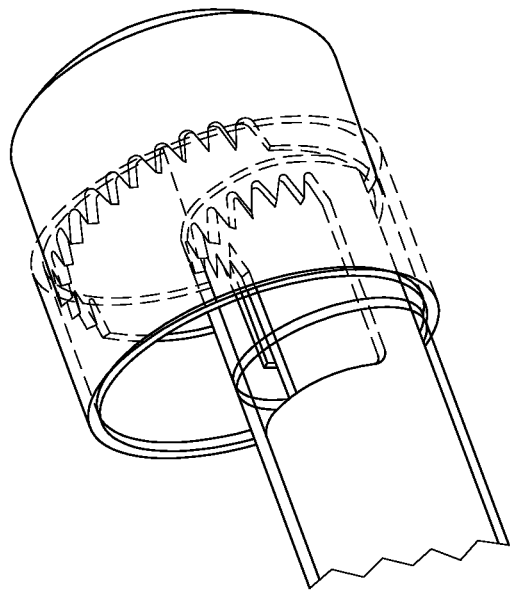
FIGS. 6A and 6B illustrate one method of use of the cutting devices of FIGS. 5A and 5B.
Figure 6A:
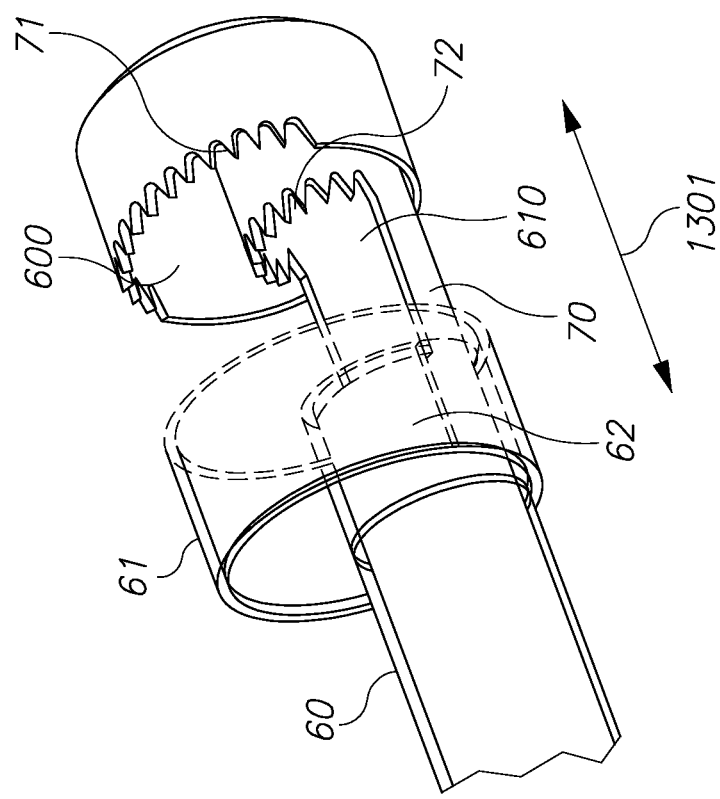

FIG. 5 shows one exemplary configuration of distal shaft member 50. As can be seen in FIG. 5B, an external shaft tube 54 is configured to accommodate internal shaft member 55 in a slidable configuration. A first external cavity is defined by external blades 51 and 52 and a second internal cavity is defined by internal blades 530 and 531, best seen in FIG. 5A. Blades 510, 520, 530 and 531 are configured to hold and cut tissue masses. Such blade members may be plain and/or serrated. As can be seen in FIG. 6A, external and internal blades 71 and 72 respectively, are rigidly connected to inner shaft 70 and are configured to move with it along the X axis 73. Addition external and internal blades 61 and 62 respectively, are rigidly connected to outer shaft 60 and are configured to move with it along the X axis 1301. It is the relative movement of inner shaft 70 and outer shaft 60 which hold and cut the tissue both in the external cavity 600 and internal cavity 610. FIG. 6B shows the closed configuration of cavities 600 and 610. A negative pressure pump is configured to create negative pressure within the inner cavity 610 in order to pull and hold tissue masses into the blades area.

According to another aspect of the embodiments described in FIGS. 1-6, the external cavity which is defined by the proximal blade 51 and distal blade 52 shown in FIG. 5, reduces the impulsion force a tissue mass experiences due to the flow of irrigating fluid delivered by irrigation outlet ports. This impulsion force works on the tissue mass in an opposite direction to that required in order to get effective morcellation because it tends to push a tissue mass away from the morcellation cavity. Dealing with this problem often consumes valuable time during the procedure. Blade 51, by reason of it having a diameter which is larger than that the diameter of the working channel of the endoscope, masks or shields at least some of the direct impulse fluid force created by the fluid inlet ports 13a, 13b of the irrigation system which is applied to a tissue mass. It should be mentioned that according to an aspect of the invention, a wideangle camera may be used to view the surgical site so that external blade 51 will not block the field of view of visualization system utilized channel 12.

During a morcellation procedure, the morcellator is configured to extend out of the distal end of the endoscope so that distal tip of shaft member 141 does not block the field of view of channel 12.

Figure 7C:
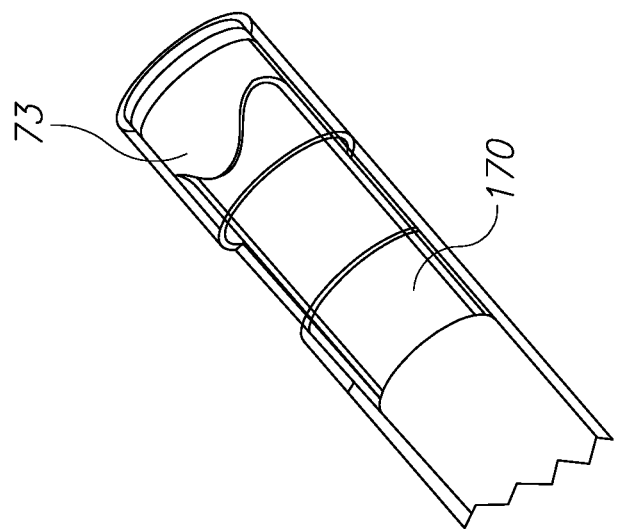
FIGS. 7A, 7B and 7C illustrate three blade embodiments of the morcellator of the present invention.
Figure 7B:
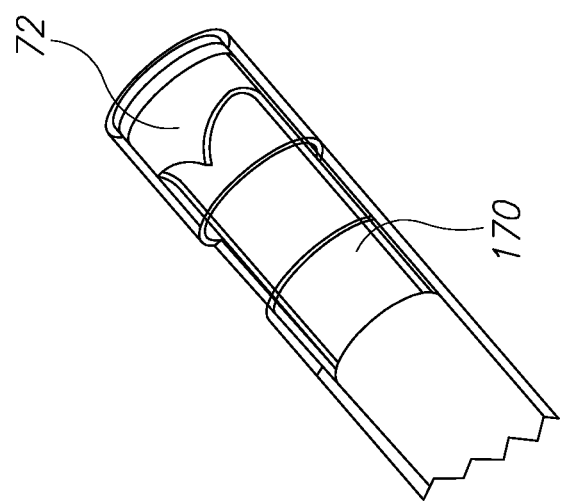
Figure 7A:
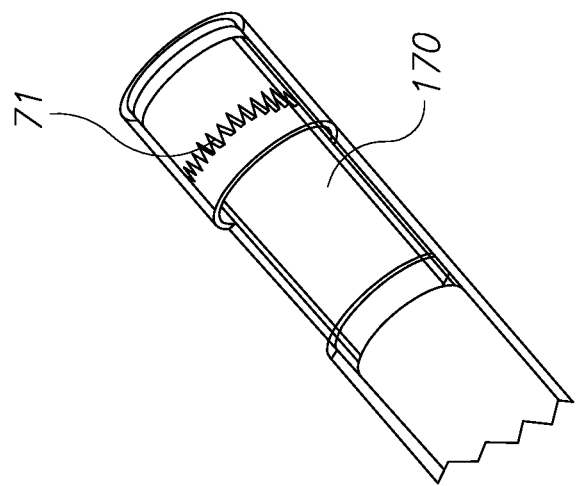
Figure 8D:
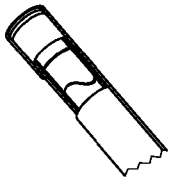
Figure 8D:
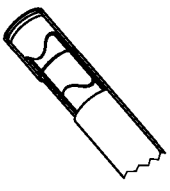
Figure 8D:
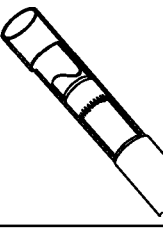
Figure 8D:
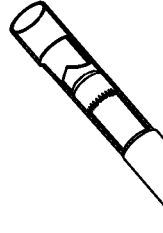

Referring now to FIGS. 7A, 7B and 7C, shown are three blade embodiments, and including serrated teeth 71, sharp teeth 72 and rounded teeth 73 respectively. As can be seen in these three non-limiting examples, each of the blades in FIGS. 7A, 7B, and 7C works against a planar or straight opposite blade 170. It should be mentioned that according to this aspect of the invention, the opposite blade may not necessarily be planar or straight and can also be any of the geometries described in FIG. 7. Referring now to FIGS. 8A, 8B, 8C and 8D shown are experimental results of different blade geometries and different blade pairings and different cavity sizes.

Referring now to FIG. 9-15 shown are different grasping solutions for tissue masses. These are designed to hold a tissue mass during morcellation and to create a positive force to push a tissue mass against the moving blades. This mechanical manipulation is in addition to the negative pressure pulling force applied on a tissue mass by the vacuum discussed above.

Figure 9:
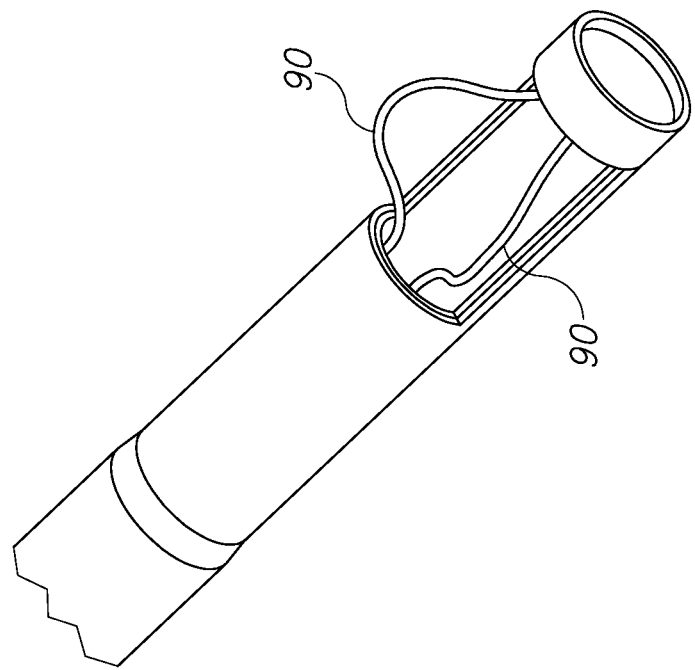
Figure 9:
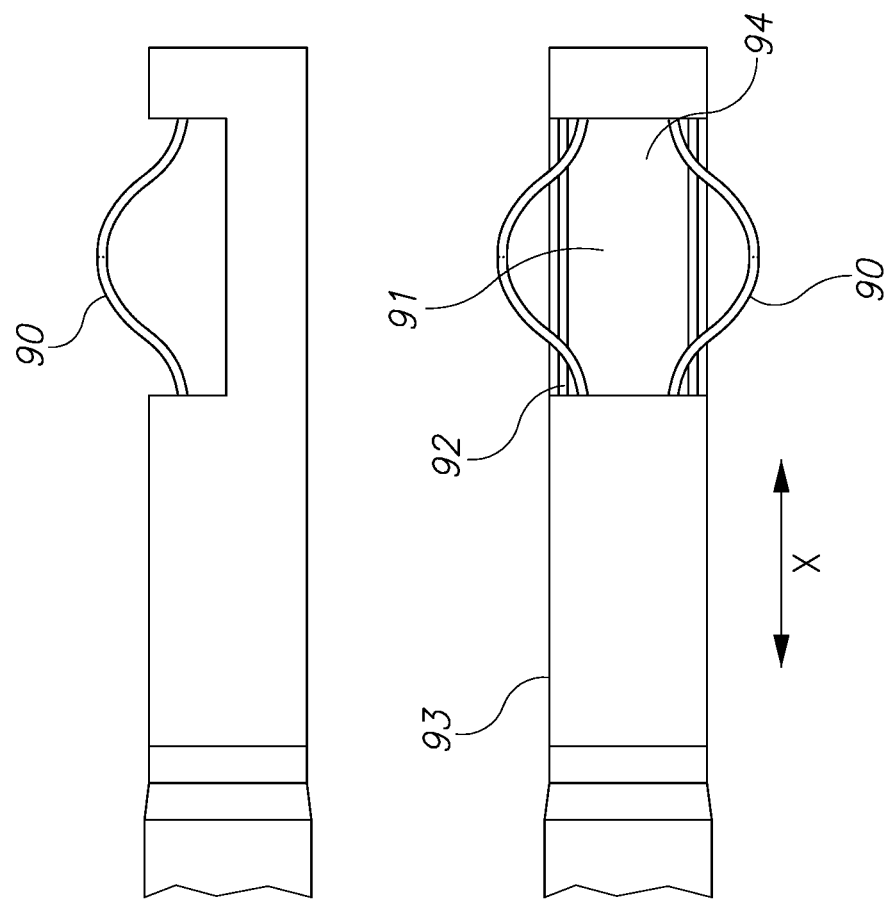

FIG. 9 illustrates a pair of flexible wires 90 made of a memory shape material, such as nitinol, which are connected to inner tube 91 and are configured to move with it along the X axis. During morcellation, inner tube 91 slides linearly inside outer tube 93 along X axis. This movement opens and closes cavity 94. During a closing movement, as wires 90 hit edge 92 of outer tube 93 they tend to bend inside outer tube 93 and therefore to create a positive force against a tissue mass which is trapped between wires 90.

Figure 10:
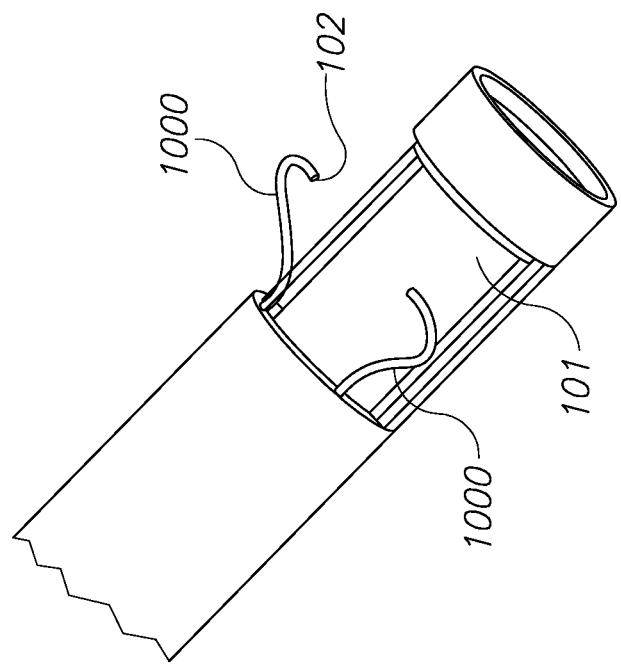
Figure 10:
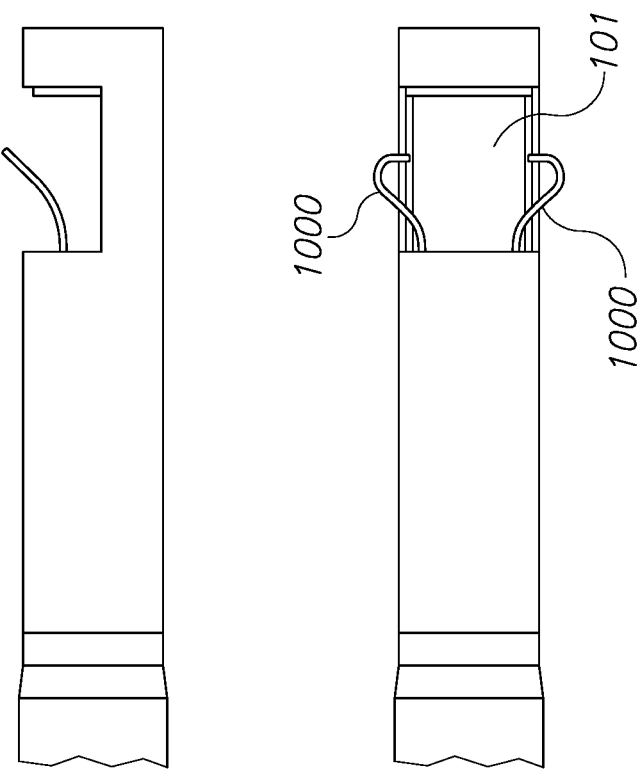

FIG. 10 shows another version of a similar solution to that in FIG. 9 in which wires 1000 are only connected to inner tube 101 in one side and are configured to grasp a tissue mass on its collapsible free edges 102.

Figure 11:
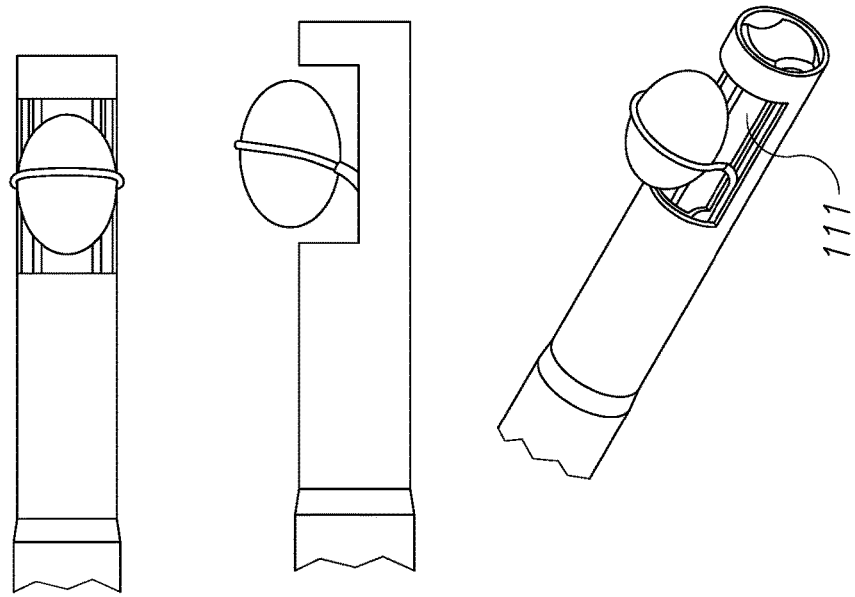
Figure 11:
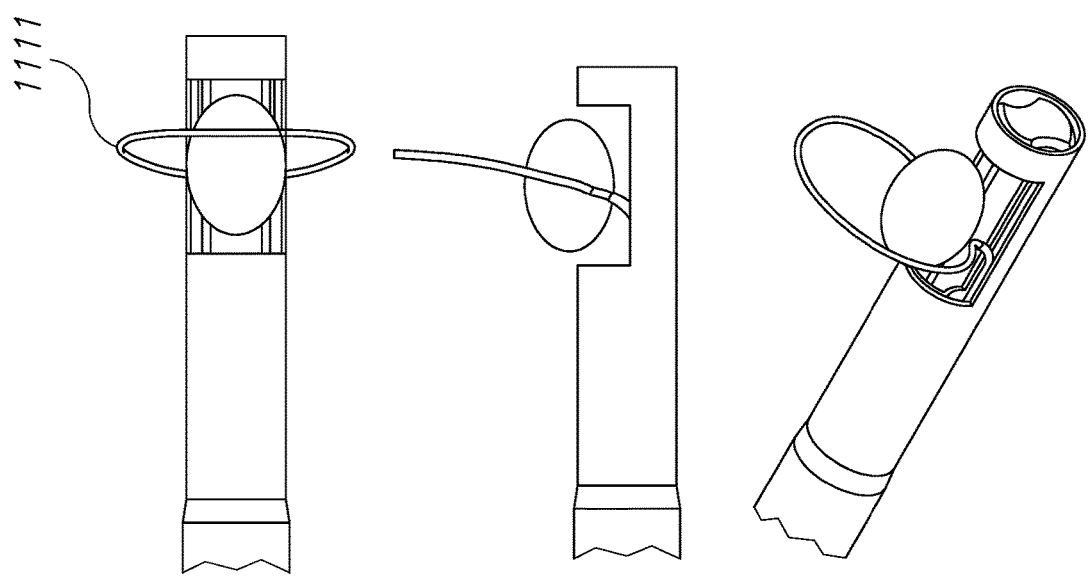

FIG. 11 illustrates another version of a similar collapsing shaped memory wire which is connected as a loop structure 1111 to inner tube 111.

Figure 12:
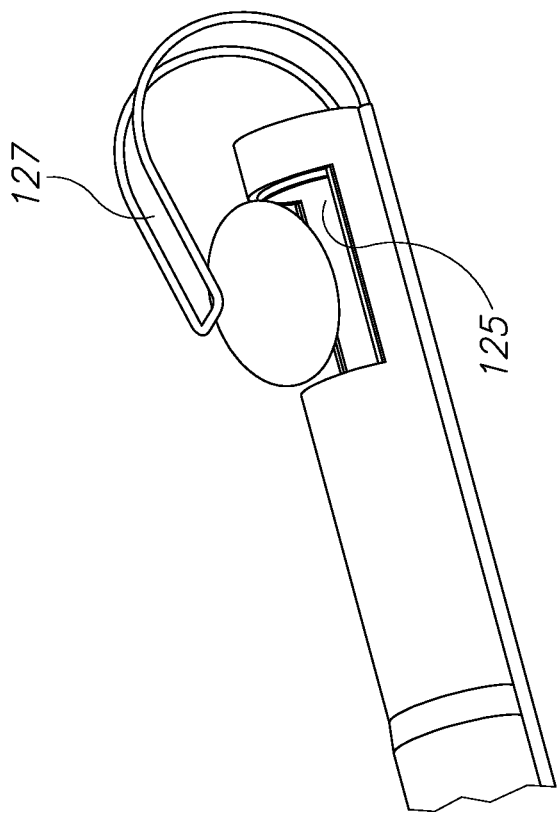
Figure 12:
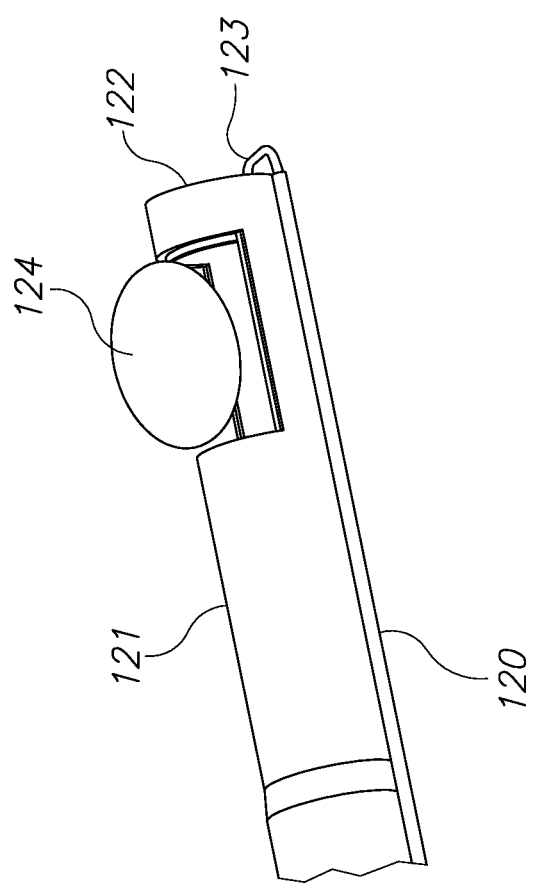

FIG. 12 illustrates an external tube 120 which is located along outer tube 121 and is configured to accommodate a slidable shaped memory wire 123. In its folded position, wire 123 runs around and adjacent morcellator tip 122. In its unfolded position, wire 123 which is made of a memory shaped material, is configured to create a loop 127 having a scorpion-tail shape, which is configured to hold and push tissue mass 124 into and against cavity 125. Wire 123 may be handled manually or automatically from the handpiece. The ability to control and manipulate from the handpiece wire 123, or any other grasping and tissue pushing element disclosed herein, improves the ability to hold and push tissue masses having different sizes and geometry. FIG. 15 shows another design.

Figure 13:
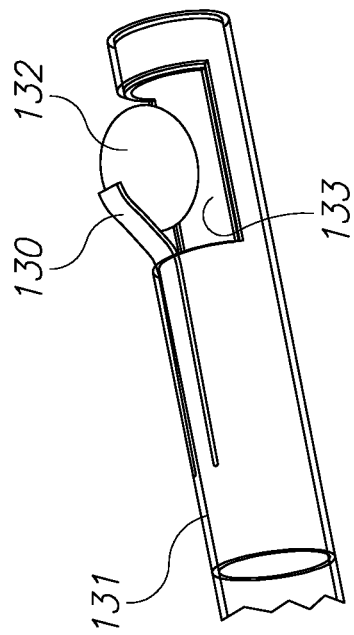
Figure 13:
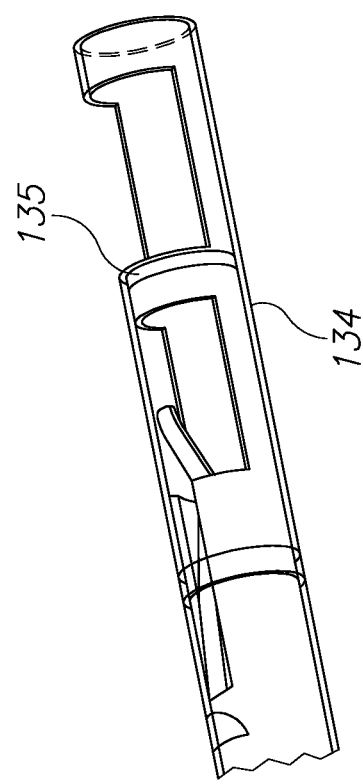

FIG. 13 illustrates another version of a collapsible element made of a memory shaped material which is configured to create a positive pressure on a tissue mass. According to this embodiment, a leaf spring 130 is attached to inner tube 131. Leaf spring 130 is configured to hold a tissue mass 132 and push it toward cavity 133. While inner tube 131 moves in outer tube 134, leaf spring 130 hits edge 135 of outer tube 134 and further pushes tissue mass 132 toward cavity 133 and the morcellator blades assembly.

Figure 14:
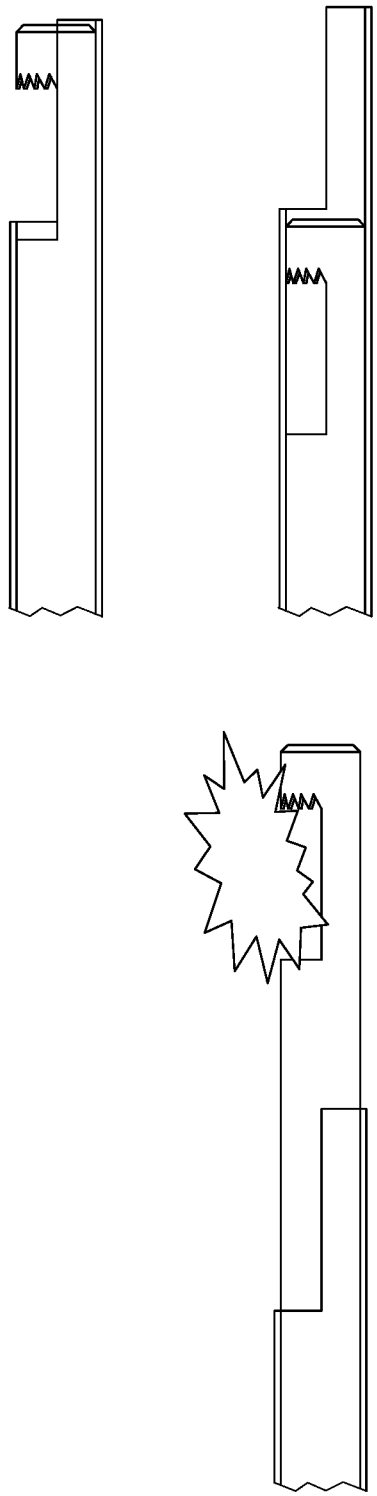

FIG. 14 illustrates yet another embodiment of the present invention in which the inner tube has an extension to manually grasp a tissue segment (augmented by suction) and bring it back towards the cutting edge as shown, after which the segment is enclosed within the inner tube recess and removed from the body as in previous embodiments.

Figure 15A:
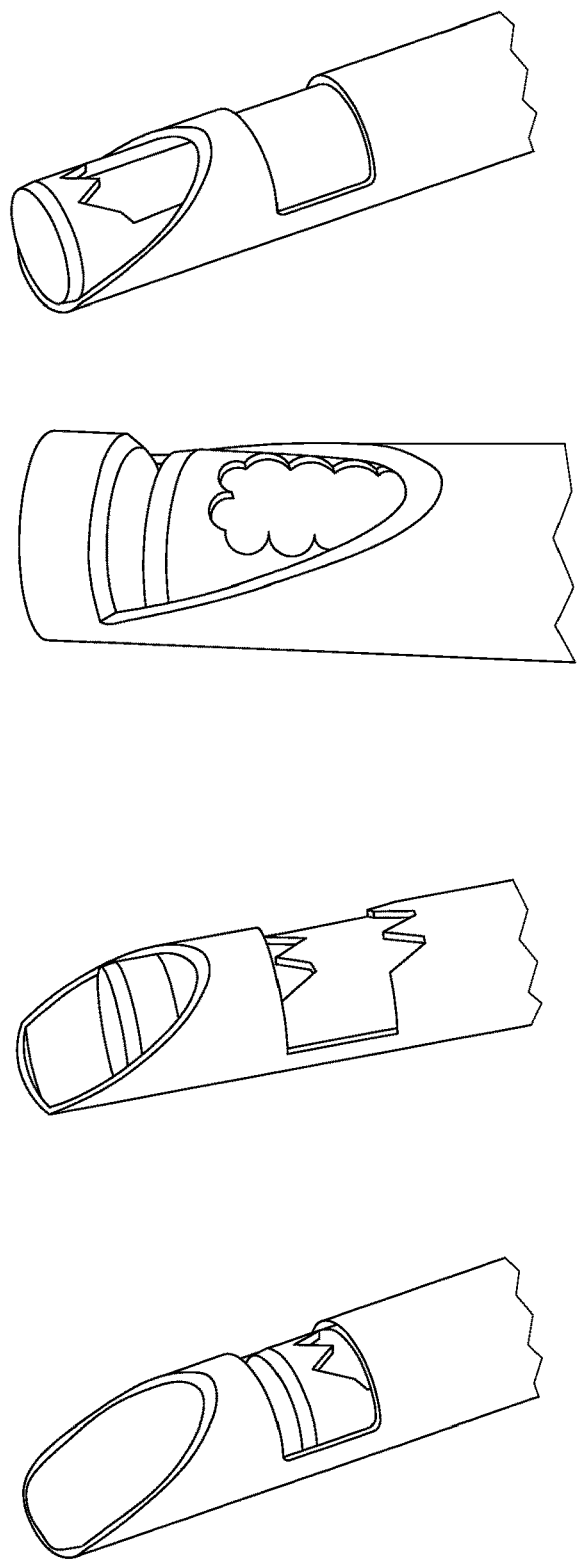

FIG. 15A illustrates a series of further embodiments of grasping and cutting implements.

Figure 15B:
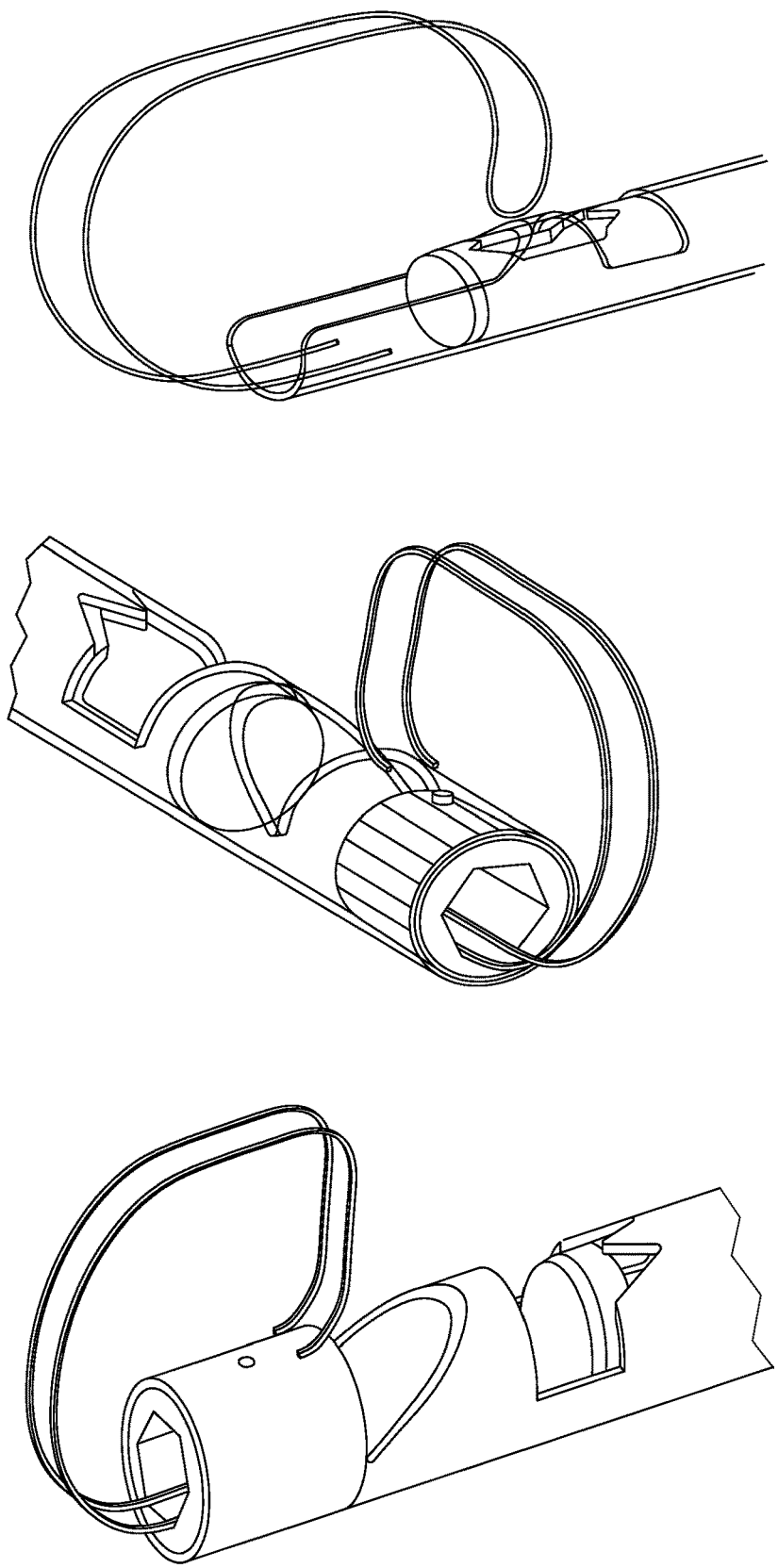

FIG. 15B illustrates a further embodiment of a tissue grasping device mounted on the distal portion of the device.

Figure 15C:
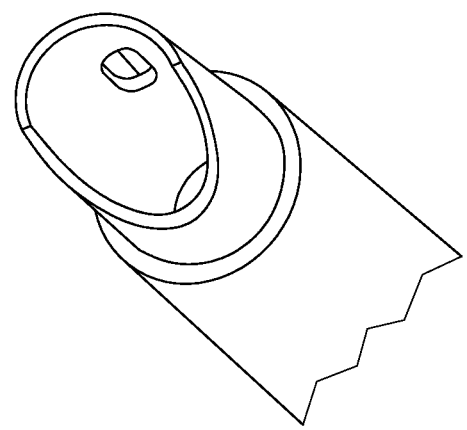
Figure 15C:
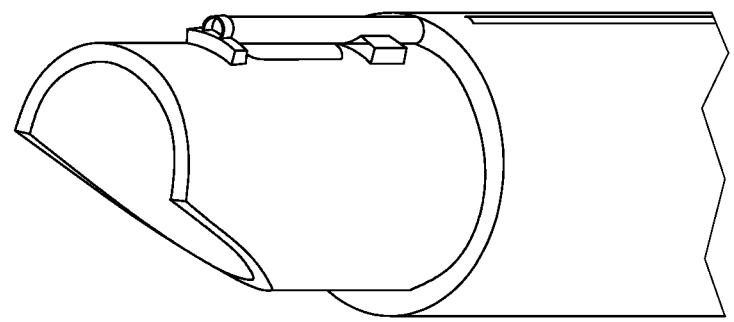
Figure 15C:
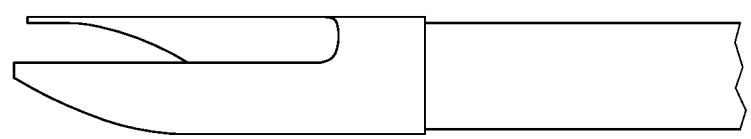

FIG. 15C illustrates further details of the distal portion of the device of the present invention.

What we claim is:

1. A device for selectively grasping and cutting tissue comprising:
    an outer tube having a longitudinal axis and an open proximal end and an open distal end;
    an inner tube within the outer tube, the inner tube having a longitudinal axis and an open distal end and an open proximal end;
    a cup-shaped cutting member mounted to the distal end of the outer tube, the cutting member being larger in diameter than the diameter of the outer tube, the cutting member including one or more cutting surfaces around the lip of the cup-shaped cutting member, the one or more cutting surfaces facing in a distal direction;
    a cylindrical cup-shaped cutting member mounted to the distal end of the inner tube; the cutting member including one or more cutting surfaces mounted around the lip of the cylindrical cup-shaped cutting member facing in a proximal direction;
    the inner tube being of a diameter to be slidably movable within the outer tube;
    whereby moving the inner tube alternately in distal and proximal directions along the longitudinal axis causes the one or more cutting surfaces of the inner tube to approach and distance themselves from the one or more cutting surfaces of the outer tube, and,
    whereby tissue situated between the inner tube and the outer tube is grasped and cut.

2. The device of claim 1 wherein the cutting surfaces on one or both of the inner and outer tubes are one of straight or serrated.

3. The device of claim 1, further comprising an endoscopic tube having a distal end and a proximal end, the endoscopic tube having a working channel having a diameter greater than that of the outer tube, whereby the proximal end of the working channel of the endoscopic tube accepts the distal end of the outer tube and the distal end of the outer tube accepts the proximal end of the inner tube through the distal end of the working channel.

4. The device of claim 3, wherein the cup-shaped cutting members of the outer and the inner tubes having a diameter no greater than that of the endoscopic tube, whereby the overall profile of the endoscopic and cup-shaped members present an overall diameter no greater than that of the endoscopic tube.

5. The device of claim 1, wherein the inner tube just proximal of the cup-shaped cutting member includes a cutout cavity along the longitudinal axis of the inner tube, further comprising a second cutting surface facing in a proximal direction within the cutout to grasp and cut tissue with the cutout.

6. The device of claim 5, wherein the second cutting surface is one of straight or serrated.

7. The device of claim 1, wherein the outer tube just distal of the cup-shaped cutting member includes a cutout along the longitudinal axis of the inner tube, further comprising a grasping device which grasps and holds tissue during cutting by moving the inner tube in a proximal direction along its longitudinal axis.

8. The device of claim 7, wherein the grasping device includes a one or pair of wires which engage and hold tissue portion prior to and during cutting by the one or more cutting surfaces on the inner and outer tubes.

9. The device of claim 7, wherein the grasping device includes a looped wire that grasps and holds a tissue portion prior to and during cutting by the one or more cutting surfaces on the inner and outer tubes.

10. The device of claim 1, further comprising a vacuum device which pulls tissue into the inner tube cavity.

11. A method of grasping and cutting tissue comprising the steps of:
    providing an outer tube having a longitudinal axis and an open proximal end and an open distal end;
    providing an inner tube within the outer tube, the inner tube having a longitudinal axis and an open distal end and an open proximal end;
    providing a cup-shaped cutting member mounted to the distal end of the outer tube, the cutting member being larger in diameter than the diameter of the outer tube, the cutting member including one or more cutting surfaces around the lip of the cup-shaped cutting member, the one or more cutting surfaces facing in a distal direction;
    providing a cylindrical cup-shaped cutting member mounted to the distal end of the inner tube; the cutting member including one or more cutting surfaces mounted around the lip of the cylindrical cup-shaped cutting member facing in a proximal direction;
    the inner tube being of a diameter to be slidably movable within the outer tube;
    moving the inner tube alternately in distal and proximal directions along the longitudinal axis, the moving causing the one or more cutting surfaces of the inner tube to approach and distance themselves from the one or more cutting surfaces of the outer tube, and,
    whereby tissue situated between the inner tube and the outer tube is grasped and cut.

12. The method of claim 11, further comprising the step of employing a vacuum device to pull tissue into the inner tube cavity.

* * * * *